(12) United States Patent
Poddar et al.

(10) Patent No.: US 10,080,379 B2
(45) Date of Patent: Sep. 25, 2018

(54) ZINC AND COPPER FORTIFYING COMPOSITION, A HYDRATING SUPPLEMENT, AND PROCESS FOR PREPARING THE SAME

(75) Inventors: Pradeep Poddar, Mumbai (IN); Henry Hidell, Hingham, MA (US); C. E. Agro, Oakville (CA); Michael Collette, Oakville (CA)

(73) Assignee: Tata Global Beverages Ltd., Kolkata (IN)

( * ) Notice: Subject to any disclaimer, the term of this patent is extended or adjusted under 35 U.S.C. 154(b) by 595 days.

(21) Appl. No.: 13/825,773

(22) PCT Filed: Sep. 23, 2011

(86) PCT No.: PCT/IN2011/000675
§ 371 (c)(1),
(2), (4) Date: Mar. 22, 2013

(87) PCT Pub. No.: WO2012/038988
PCT Pub. Date: Mar. 29, 2012

(65) Prior Publication Data
US 2013/0287897 A1    Oct. 31, 2013

(30) Foreign Application Priority Data
Sep. 23, 2010 (IN) ............................ 1072/KOL/2010

(51) Int. Cl.
*A23L 2/52* (2006.01)
*A23L 1/304* (2006.01)
*A61K 33/14* (2006.01)
*A61K 33/34* (2006.01)
*A61K 33/30* (2006.01)
*A23L 33/16* (2016.01)

(52) U.S. Cl.
CPC ............... *A23L 1/304* (2013.01); *A23L 2/52* (2013.01); *A23L 33/16* (2016.08); *A61K 33/14* (2013.01); *A61K 33/30* (2013.01); *A61K 33/34* (2013.01); *A23V 2002/00* (2013.01); *A23V 2250/1642* (2013.01)

(58) Field of Classification Search
CPC . A23L 1/304; A23L 2/52; A23L 33/10; A61K 33/30; A61K 33/34; A61K 33/10
USPC ........................................ 426/2, 66, 74, 648
See application file for complete search history.

(56) References Cited

U.S. PATENT DOCUMENTS

| | | | |
|---|---|---|---|
| 5,389,360 A * | 2/1995 | Mobley et al. | ................. 424/49 |
| 6,030,605 A * | 2/2000 | D'Ameila et al. | ............. 424/48 |
| 6,413,558 B1 | 7/2002 | Weber et al. | |
| 6,451,341 B1 | 9/2002 | Slaga et al. | |
| 6,458,981 B1 * | 10/2002 | Ashmead | .............. C07C 227/16 556/116 |
| 6,475,539 B1 * | 11/2002 | DeWille | .................... A23L 2/38 426/573 |
| 7,341,708 B1 * | 3/2008 | Miroshnychenko | . A61K 31/195 424/1.11 |
| 2002/0102220 A1 * | 8/2002 | Stephenson | ..................... 424/49 |
| 2002/0122843 A1 * | 9/2002 | McGrew | ................ A23G 4/046 426/3 |
| 2002/0122847 A1 | 9/2002 | Nunes et al. | |
| 2003/0049352 A1 * | 3/2003 | Mehansho et al. | ............. 426/66 |
| 2003/0077333 A1 * | 4/2003 | Phillips | .............. A61K 31/7004 424/643 |
| 2003/0211204 A1 | 11/2003 | Fields et al. | |
| 2004/0058034 A1 | 3/2004 | Mehansho et al. | |
| 2004/0161504 A1 | 8/2004 | Daniels et al. | |
| 2008/0118574 A1 | 5/2008 | Mueller et al. | |
| 2010/0166916 A1 | 7/2010 | Lawson et al. | |
| 2012/0042893 A1 * | 2/2012 | Campbell et al. | ............ 132/200 |

OTHER PUBLICATIONS

NPL "zinc and copper" by Jun Ma and Nancy M. Betts entitled 'Zinc and copper intakes . . . individuals (CSFII)'in J. Nutr. 130:2838-2843, 2000.*
NPL Zinc lactate gluconate retrieved on Dec 23, 2013.*
NPL Copper bis glycinate, retrieved on Aug. 31, 2014.*
NPL Potassium Sorbate human dose from Wikipedia Reference # 12 and WHO article (1967).*
August et al. "Determination of zinc and copper absorption at three dietary Zn—Cu ratios by using stable isotope methods in young adult and elderly subjects", Am J. Clin. Nutr. 50: 1457-1463, 1989.*
Festa et al. entitled "Effects of Zinc intake on copper excretion and retention in men" in Am. J. Clin. Nutr. 41: 285-292, 1985.*
International Search Report issued in International Application No. PCT/IN2011/000675 dated May 8, 2012; 2 pages.
Authorized Officer Philippe Becamel, PCT Preliminary Report on Patentability, PCT Application Serial No. PCT/IN2011/000675, dated Mar. 26, 2013, 6 pages.
Extended European Search Report, European Application No. EP 11826524.8, dated Feb. 20, 2014, 6 pages.

* cited by examiner

*Primary Examiner* — Bhaskar Mukhopadhyay

(74) *Attorney, Agent, or Firm* — Fish & Richardson P.C.

(57) ABSTRACT

The present invention provides nutrient zinc and copper fortifying composition for food products. More particularly the present invention provides zinc and copper fortifying composition comprising zinc lactate gluconate, copper ion source, and class II preservative. The invention further provides a hydration supplement and a fortified water beverage to supplement the deficiencies of zinc in humans.

13 Claims, No Drawings

ZINC AND COPPER FORTIFYING COMPOSITION, A HYDRATING SUPPLEMENT, AND PROCESS FOR PREPARING THE SAME

CLAIM OF PRIORITY

This application is a U.S. National Stage of PCT/IN2011/000675 filed on Sep. 23, 2011, which claims priority to and incorporates by reference Indian Patent Application No. 1072/KOL/2010 filed on Sep. 23, 2010.

FIELD OF INVENTION

The present invention provides nutrient fortifying composition, a hydration supplement and the process for preparing the same for the enhancing the well being of the nutritionally deficient humans. More particularly the present invention provides zinc and copper fortifying composition and its use in hydration supplement, more particularly the invention provides a fortified beverages.

BACKGROUND OF THE INVENTION

Micronutrients are nutrients needed throughout life in small quantities. They are dietary nutrients needed by the human body in very small quantities (generally less than 100 micrograms/day) as opposed to macro-minerals which are required in larger quantities. The Micro-nutrients or trace elements include at least iron, cobalt, chromium, copper, iodine, manganese, selenium, zinc, boron and molybdenum.

Due to urbanization, over population and ill practices of agriculture there are losses of essential minerals from the soil. Due to insufficient nutrients in soil there is a declination of nutrients in food, which in turn causes deficiency of nutrients among the subjects who consume such food. Some major consequences of such deficiencies are bone disease, in every age group.

Zinc is an essential trace element for all forms of life. The significance of zinc in human nutrition and public health was recognized relatively recently. Clinical zinc deficiency in humans was first described in 1961, when the consumption of diets with low zinc bioavailability due to high phytic acid content was associated with "adolescent nutritional dwarfism" in the Middle East.

Numerous aspects of cellular metabolism are zinc-dependent. Zinc plays important roles in growth and development, the immune response, neurological function, and reproduction. On the cellular level, the function of zinc can be divided into three categories:
1. Catalytic: Nearly 100 different enzymes depend on zinc for their ability to catalyze vital chemical reactions.
2. Structural: Zinc plays an important role in the structure of proteins and cell membranes. A finger-like structure, known as a zinc finger motif, stabilizes the structure of a number of proteins. Loss of zinc from biological membranes increases their susceptibility to oxidative damage and impairs their function.
3. Regulatory: Zinc finger proteins have been found to regulate gene expression by acting as transcription factors (binding to DNA and influencing the transcription of specific genes). Zinc also plays a role in cell signaling and has been found to influence hormone release and nerve impulse transmission. Recently, zinc has been found to play a role in apoptosis (gene-directed cell death), a critical cellular regulatory process with implications for growth and development, as well as a number of chronic diseases.

Zinc deficiencies lead to increased incidence or bigger severity of a long list of human diseases and disorders. Zinc is, inter alia, very important for maintaining the immune system of humans, including having antiviral properties. It is also required for normal brain growth and functioning. Furthermore, it is important for reducing the vulnerability of humans to diseases like malaria, pneumonia and diarrhoea, which are prevalent in many developing countries. Zinc deficiency leads to retarded growth and increased incidences of dwarfism.

Copper (Cu) is an essential trace element for humans and animals. In the body, copper shifts between the cuprous ($Cu^{1+}$) and cupric ($Cu^{2+}$) forms, though the majority of the body's copper is in the $Cu^{2+}$ form. The ability of copper to easily accept and donate electrons explains its important role in oxidation-reduction (redox) reactions and in scavenging free radicals. Copper is a critical functional component of a number of essential enzymes known as cuproenzymes. Some of the physiologic functions known to be copper-dependent are:
1. Energy production
2. Connective tissue formation
3. Iron metabolism
4. Functioning of Central nervous system
5. Neurotransmitter synthesis
6. Metabolism of neurotransmitters
7. Formation and maintenance of myelin
8. Melanin formation
9. Antioxidant functions
10. Functioning of Superoxide dismutase
11. Functioning of Ceruloplasmin
12. Regulation of gene expression Several food and beverages have been provided to supplement the deficiencies of the micro and trace nutrients in the human bodies.

Since the acute shortage of the micronutrients particularly zinc and copper causes major health problems among humans, it has been very important to supplement the same through food. To overcome these health problems fortifications have been introduced in the masses so as to provide them nutrition.

However, supplementing the micro-nutrient deficiencies through food is not always feasible due to different food habits of the subjects in different geographical locations. However, the same can be done through drinking water.

Therefore, the object of the present invention is to provide a composition of micronutrients for fortifying food & water beverages for human consumption.

Further, the object of the present invention is to provide a micro-nutrient composition comprising zinc and copper.

Further, the object of the present invention is to provide a hydrating supplement fortified with the micro nutrients to supplement the deficiencies.

Further, the object of the present invention is to provide beverage fortified with the micro nutrients to supplement the deficiencies in humans.

Yet another object of the present invention is to provide beverage fortified with Zinc and Copper to reduce the deficiencies diseases in humans.

Yet another object of the present invention is to provide an inexpensive source and additional dietary nutrients such as Zinc and copper in treated water beverage.

Further, object of the present invention is to provide the process for the preparation of the composition of micronutrients.

Further, object of the present invention is to provide the process for the preparation of the treated water beverage fortified with the micro nutrients to supplement the deficiencies.

SUMMARY OF THE INVENTION

In order to obviate the drawbacks of the prior art and to provide a suitable supplement micronutrients, the present invention provides a composition of micronutrients particularly zinc and copper for fortifying food for human consumption.

Therefore, embodiments of the present invention provides zinc and copper fortifying composition for fortifying food products. Said composition comprises:
zinc lactate gluconate,
copper ion source, and
class II preservative (202)

The percentage of amounts of the ingredients in the composition is as follows:
about 32.25% to 34.37% by wt Zinc lactate gluconate;
about 42.5% to 45.2% by wt copper ion source; and
about 18 to 22% by wt class II preservative (202)

The invention further provides a hydration supplement for human consumption. Said hydration supplement comprising the zinc and copper fortifying composition along with a suitable food item or water beverages. Further, the amount of composition in the hydration supplement is 0.0048% by weight or 48 mg per liter such that the amount of the Zinc source ingredient in the hydration supplement is 0.0015% to 0.0017% by weight and amount of copper source in the hydration supplement is about 0.00216% by weight or about 22 mg per liter.

Said hydration supplement is in liquid or semi solid or solid form. Further said hydration supplement may be a beverage such as aerated drink, treated water, etc.

One or more embodiments of the invention further provides treated water beverage fortified with Zinc and copper composition. The fortified water comprises:
treated water prepared by the process taught in our co-pending application 1069/KOL/2010,
zinc fortifying composition comprising zinc lactate gluconate, copper ion source, and class II preservative (202).

The beverage of one or more embodiments of the present invention provides essential micro-nutrients zinc (at least 3 to 4 mg per liter) and copper (0.8 to 1.2 mg per liter) from the zinc fortifying composition.

Further the water of one or more embodiments of the present invention has no added flavors or sweeteners to mask ingredient flavors. The ingredients used in the water neutral beverage are selected in a manner as to be compatible with water such that they do not have any odour. This is highly soluble and the composition does not precipitate or reacts or sediments.

Further, the Copper from the Copper source in the composition enables cold-filling process of packaging. The filling could then be carried out without the presence of ozone in the product and also obviating the necessity of hot-fill process thereby enhancing the bio-availability of Zinc from the Zinc source in the composition.

Further, because zinc can block copper absorption, it is important that it be supplemented by additional amounts of copper.

The ratio of the elemental Zinc to the Copper is maintained at 3:1 in the said composition as well as the hydration supplement.

Also, the shelf life of the elements has been so maintained in the composition that when the composition does not degrade when used with water. Said effects are the result of the synergistic effect among the ingredients of the composition.

The invention further provides the process for the preparation of the treated water beverage fortified with zinc and copper.

DETAILED DESCRIPTION OF THE INVENTION

The present invention has been made by keeping an idea to ameliorate the nutritional level of the large deficit population. These populations are affected with most prevalent immunity disorder caused due to the imbalance in zinc and anemia due to copper's inadequate intake and hence their concentration in the body. Zinc helps the human body to fight against many infectious diseases and cancer, & copper reduces anemia. The amount added is equivalent to at least 3 to 4 mg of elemental zinc and about 0.8 to 1.2 mg of elemental copper per 1000 ml of water. The intention of this kind of fortified product is to provide an inexpensive source for safe drinking water by additional dietary zinc for the immune disordered and anemic population. Due to the insufficiency of zinc and copper in the population as well as in the populations worldwide, the fortified water beverage of the present invention will be a beneficial and cost-effective strategy to combat the disorders.

Functions of Zinc in Human Body

Our body contains 2-3 gm of zinc, which plays many diverse roles in enabling healthy growth and development and in promoting good health in general hence is essential for life of an organism. The body needs it in many ways as to:
enable the activity of more than 200 biological enzymes
help in the synthesis of proteins and genetic materials
involves in the metabolism of carbohydrates, lipids & energy
have normal body growth and maintenance of muscles & helps in skeletal development
stimulate hair growth
develop taste perception
assist in hormonal activity, reproduction and lactation It plays a key role in keeping immune system healthy, which protects the body against infection and cancer. Zinc is found throughout the body 60% in muscles, around 30% in bones and the rest in our skin, hair etc.

Men require zinc ⅓ higher than a women because male semen contains 100 times more of the zinc as it is found in the blood.

Many of the factors hinder the absorption of zinc due to which the real absorption remains at 20% of the total zinc intake.

Zinc has certain recommended limit, up to that it is useful otherwise deficiency or toxicity happens.

How Much Zinc is Required in Humans?

Intake recommendations for zinc is provided in the Dietary Reference Intakes (DRIs) developed by the Food and Nutrition Board (FNB) at the Institute of Medicine (IOM) of the National Academies (formerly National Academy of Sciences). DRI is the general term for a set of reference values used for planning and assessing nutrient intakes of healthy people.

The amount of Zinc recommended is 10 mg/day (Women) to 12 mg/day (Man) for an adult in India has been established by National Institute of Nutrition, Hyderabad (NIN). Mean absorption and the loss of zinc valued 34.5% and 1.7 mg respectively.

The current RDAs for zinc are listed in Table 1. For infants' aged 0 to 6 months, the FNB established an AIs for Zinc that is equivalent to the mean intake of zinc in healthy, breast fed infants.

TABLE 1

Recommended Dietary Allowances (RDAs) for Zinc

| Age | Male | Female | Pregnancy | Lactation |
|---|---|---|---|---|
| Birth to 12 months | 2 mg* | 2 mg* | — | — |
| 1 to 9 years | 5 mg | 8 mg | — | — |
| 10 to 12 years | 9 mg | 9 mg | — | — |
| 13 to 15 years | 11 mg | 11 mg | — | — |
| 16 to 17 years | 12 mg | 12 mg | 13 mg | 14 mg |
| 19+ years | 10 mg | 12 mg | 12 mg | 12 mg |

*Adequate Intake (AI)

In India adult male requires 12 mg/day whereas 10 mg/day has been taken by the females (at the pregnancy & lactating stages they require 12 mg per day).

Large amount of zinc taken may cause nausea and diarrhea. An elevated amount for example 1-2 gm per day for regular basis will harm immune system. Zinc interferes in the absorption of iron and copper so it is recommended to take it at night after a gap between the supper & its dose but should not be taken empty stomach.

Because zinc can block copper absorption, it is important that it be supplemented by additional amounts of copper.

The U.S. Food and Nutrition Board set the tolerable upper limit for adults at 40 mg/day including dietary and supplement zinc.

Dietary Sources of Zinc

Oysters contain more zinc per serving than any other food, but red meat and poultry provide the majority of zinc in the American diet. Lean red meat, whole-grain cereals, pulses, and legumes provide the highest concentrations of zinc 25-50 mg/kg (380-760 mmol/kg) raw weight but phytates, which are present in these foods, bind zinc and inhibit its absorption. Thus, the bioavailability of zinc from grains and plant foods is lower than that from animal foods, although many grain & plant based foods are still good sources of zinc.

Other good food sources include beans, nuts, certain types of seafood (such as crab and lobster), fortified-breakfast cereals, and dairy products.

Pumpkinseeds provide the best source for zinc for vegetarians & others include dairy products, yeast & lentils.

Vegetarians require 50% more of the Zinc amount than non-vegetarians as its bioavailability through plants is much less than meat.

Interest in Zinc Fortified Products

Much of the zinc is destroyed in processing of foods, so an additional amount is required to reduce the symptoms occurring due to its insufficiency. Sometimes it is been lost in the cooking too so people's diet is declining in zinc concentration. Too little of zinc in the body creates problems such as stunted growth in children, hair loss, the sense of smell suffers, diarrhea, delayed wound healing. Men with shortage of zinc decrease their fertility & women experience irregular periods.

Zinc Lactate Gluconate

Zinc Lactate Gluconate is the organic zinc complexes, which liberate the organic acids such as Lactic acid & Gluconic acid.

Zinc Gluconate $C_{12}H_{22}O_{14}Zn$ is a zinc salt of gluconic acid, has proven to be best remedy for cold. Divalent Zinc has a good bioavailability and has a good balance between solubility and flavor.

Due to the major involvement of zinc in more than 300 enzymatic functions make it valuable for human development and maintenance. Zinc deficiency may occur due to inadequate intake, mal-absorption, increased losses & impaired utilization. All the above mentioned problems require an extra amount of zinc to combat their effect. Infants and growing children are at high risk of zinc deficiency followed by adults, pregnant & lactating women, and elderly people. These adverse effects require some measurements to lessen them and to make nutrition healthier regarding micronutrient, zinc. Fortified products coming in the market can help reduce the severe effect by giving the affected population an additional quantity of zinc.

Functions of Copper in Human Body

Copper plays a significant role in human physiology. Copper is utilized by most cells as a component of enzymes (cuproenzymes) essential for many biochemical functions to occur normally in human body. Copper is a major component of catalytic center with Zinc superoxide dismutase in different redox reactions in the enzymes and thus its presence is important for normal physiological functions.

Functions of cuproenzymes with oxidation-reduction activity and copper binding proteins in human are given in table 2.

TABLE 2

Function of cuproenzymes in oxidation and reduction activity of human

| Cuproenzymes | Important functions |
|---|---|
| Amino acid oxidase | Amino acid metabolism i.e. Deamination of primary amines |
| Ceruloplasmin | Copper transport, conversion of iron into active form for transportation to various tissues. |
| Cytochrome-C oxidase | Energy production |
| Catechol oxidase | Synthesis of melanin |
| Dopamine-β monooxygenase | Noradrenaline synthesis |
| Protein-lysine 6-oxidase | Collagen and elastin cross-linking |
| Peptidylglycine monooxygenase | a-Amidation of neuropeptides |
| Superoxide dismutase | Protection of cell from free redical damage |
| Superoxide dismutase & lysyl oxidase | Strengthens connective tissues |
| Metallothionein | Radical scavenging, Metal transport |

Thus, vital role played by copper in the human body includes the following.

1. Formation of strong, flexible connective tissue and helps in the proper cross linking of collagen and elastin. Elastin helps to promote normal cardiovascular functions.
2. Production of collagen—the protein responsible for the structural formation of bone, cartilage, skin & tendon: prevents bone problems such as arthritis, osteoporosis, and rheumatoid arthritis.
3. Inhibition of free radical formation.
4. Formation of adenosine triphosphate (ATP) the fuel to run the body.
5. Production of hemoglobin thus helping to prevent anemia4.

6. Promotes the maintenance of good skin health and contributes to healthy respiration and general strength.
7. Contributes to healthy and normal cholesterol levels.
8. Excellent for immune system.

How Much Copper do Human Need?

The average adult human body generally contains 50-80 mg of copper. Recommended dietary allowance (RDA) for copper is shown in Table 3 as per The Food and Nutrition Board, Institute of Medicine, National Academies.

TABLE 3

Recommended dietary allowance (RDA) of copper for human

| | Copper, μg/day | |
|---|---|---|
| Life stage | Male | Female |
| Infants | | |
| 0-6 months | 200* | 200* |
| 7-12 months | 220* | 220* |
| Children | | |
| 1-3 years | 340 | 340 |
| 4-8 years | 440 | 440 |
| 9-13 years | 700 | 700 |
| 14-18 years | 890 | 890 |
| Adults | | |
| 19-30 years | 900 | 900 |
| 31-50 years | 900 | 900 |
| 51-70 years | 900 | 900 |
| >70 years | 900 | 900 |
| Pregnancy | | |
| 14-18 years | — | 1000 |
| 19-30 years | — | 1000 |
| 31-50 years | — | 1000 |
| Lactating | | |
| 14-18 years | — | 1300 |
| 19-30 years | — | 1300 |
| 31-50 years | — | 1300 |

*is the Adequate Intakes and the rest are the Recommended Dietary Intakes as per given by FNB Copper can be quite toxic when introduced into a living system in amounts that exceed the system's ability to render the metal safe through binding proteins or other means. Infants fed with cow milk based diets exclusively are more prone to develop copper deficiency than infants who are breast fed because of the low copper content of cow milk and limited absorption of this mineral in cow milk. While the milk stored and boiled in the copper utensils is sometimes toxic and in India this decline in copper found when copper vessels are avoided for these kinds of uses.

Dietary Sources of Copper

Copper is found in number of food items, originating from both plants as well as animals. The plants or the plant parts normally rich in copper are nuts, seeds, whole grains, legumes, chocolates, cherries, dried nuts, root vegetables, cereals, peas, beans, tomatoes, milk, tea, potatoes while the food originating from animal source rich in copper are such as organ meat, chicken, seafood etc. Drinking water delivered through copper plumbing is a minor source of copper. It has long been established since the ancient times and the times of Ayurveda that drinking water when kept and taken from copper vessels is a cure for several ailments. For the same reason copper pipes were used for plumbing for delivering drinking water in many Middle East countries.

Interest in Copper Fortified Product

Deficiency of Copper Causes:
  Anemia
  Nutropenia
  Bone abnormalities in low birth weight in infants & in young children; fractures, osteoporosis, epiphyscal separation, fraying and cupping of metaphyses with spur formation and subperiostal new bone formation.

Copper Ion Source

Copper in the cupric ($Cu^2$) state is believed to be readily absorbable and efficiently transported across cellular membranes. The ions also provide a unique product stabilizing residual anti microbial efficacy for beverages that retards the growth of bacteria & other microorganisms including *Salmonella, Fungi, Coliforms, Vibriocholera*. This unique efficacy is residual and occurs during the growth of the microorganisms.

Copper intake tends to be low in Indian population due to certain reasons such as unawareness of the essentiality of this mineral amongst masses, improper diets, geographical imbalance and many more. Providing a safe, inexpensive bottled drinking water with a modest amount of copper added is likely to be beneficial in improving copper intakes. The amount of copper proposed for this product is modest 0.1 mg per 100 ml of water. The proposed copper for source for this product is Nutribond, which appears to be an ingredient with appropriate bioavailability, solubility and neutral taste. Said Nutribond Copper comprises Copper Sulphate as a source of Copper alongwith Ammonium Sulphate. Said Copper Sulphate is in the form of Copper Sulphate Pentahydrate. Further, it comprises Food grade Acidic compounds to maintain Copper in its potent ionic form.

Therefore, in order to prevent and bring down the occurrence of its deficiency diseases, it is necessary to supplement the daily food by providing additional quantities of the nutrients and this can be best done by way of fortification of a product of major consumption.

The present invention provides composition of micronutrients for fortifying food and water beverage products with Zinc. Said composition comprises:
  zinc lactate gluconate,
  copper ion source, and
  Class II preservative (202)

The percentage amount of the ingredients in the composition is as follows:
  about 32.25% to 34.37% by wt Zinc lactate gluconate
  about 42.5% to 45.2% by wt Copper Ion Source
  about 18 to 22% by wt class II preservative (202)

The composition of the present invention can be used as nutrient supplement in food items such as beverages, snacks, powered milk, etc. depending upon the nutrient requirement the composition of the present invention can be added in the food items.

In another embodiment the invention provides a hydration supplement for human consumption. Said hydration supplement comprising the zinc fortifying composition along with a suitable food item. Further, the amount of composition in the hydration supplement is 0.0048% by weight or 48 mg per liter such that the amount of the Zinc source ingredient in the hydration supplement is 0.0015% to 0.0017% by weight and amount of copper source in the hydration supplement is 0.00216% by weight or about 22 mg per liter.

Said hydration supplement is in liquid or semi solid form. Further said hydration supplement may be a beverage such as aerated drink, treated water, etc.

In yet another embodiment the invention provides treated water beverage fortified with this Zinc and copper composition. The fortified water comprises:
- treated water prepared by the process taught in our co-pending application,
- Safe composition comprising zinc lactate gluconate, copper ion source, potassium sorbate class II preservative (202)

The beverage of the one or more embodiments of the present invention provides essential micro-nutrients zinc (3 to 4 mg per liter) and copper (0.8 to 1.2 mg per liter) from the Tata Water Plus Safe Blend. The preferable amounts zinc is 3 mg/liter and that of copper is 1 mg/liter as provided in Table 4 and 5 shows the amounts of nutrients per liter of water.

TABLE 4

| Ingredients | (in 1 liter) | | Active Ingredients per liter |
|---|---|---|---|
| Zinc Lactate Gluconate | 16.5 mg | delivers | 3 mg Zinc |
| Nutribond ™ Copper Ion | 21.5 mg | delivers | 1 mg of Cu |

TABLE 5

| | Quantity (per liter) | RDA - India | % of RDA in one liter | Safe Upper level per day (Supplementation) | Source | Validation |
|---|---|---|---|---|---|---|
| Zinc | 3 mg | 10 mg | 30% | 25 mg | Expert group of vitamins & Minerals, UK - 2003 (Article encl). | Zinc affects iron and copper uptake at supplemental doses of 50 mg/day and above. No risk of toxicity at 50 mg Zinc per day supplementation. Higher dose could adversely impact the gastro intestinal system in people as validated in human trials - Expert Group UK. Since zinc is not stored, the balance between absorption and excretion (homeostasis) is essential to the maintenance of a broad spectrum of zinc-dependent functions. |
| Copper | 1 mg | 2 mg | 50%* | 10 mg | Expert group of vitamins & Minerals, UK - 2003 (Article encl) | Exceeds the unstated upper limit of 33% of RDA for 'non supervised' fortification as per PFA (Re Dr. Seshikeran). However, as per pfa standards elemental copper upto 1 mg per liter is allowed for natural mineral water confirming that this level is safe for consumption in water. Study reports on Copper toxicity and storage in human systems have established a safe upper limit of 10 mg/day in a 60 kg adult |

*exceeds the unstated upper limit of 33% of RDA for 'non supervised' fortification as per PFA (Re Dr. Seshikeran). However, as per pfa standards elemental copper up to 1 mg per liter is allowed for natural mineral water confirming that this level is safe for consumption in water.

Further the water of one or more embodiments of the present invention has no added flavors or sweeteners to mask ingredient flavors. The ingredients used in the water neutral beverage are selected in a manner as to be compatible with water such that they do not have any odour, the composition does not precipitate or reacts or sediments. Also, the shelf life of the elements has been so maintained in the composition that when the composition does not degrade when used with water. Said effects are the result of the synergistic effect among the ingredients of the composition.

Further, the Copper from the Copper source in the composition enables cold-filling process of packaging. The filling could then be carried out without the presence of ozone in the product and also obviating the necessity of hot-fill process thereby enhancing the bio-availability of Zinc from the Zinc source in the composition. Further, because zinc can block copper absorption, it is important that it be supplemented by additional amounts of copper.

The product of the present invention is used for enhancing the well-being of the Indian consumer where certain nutritional deficiencies can be targeted. This provides a safe, inexpensive water beverage fortified with modest levels of micro-nutrients, beneficial in improving the health status of those suffering from Zinc deficiencies.

In yet another embodiment the present invention provides the process for the preparation of the treated water beverage fortified with zinc and copper.

Said process comprises the steps of:
- preparing treated water in accordance with the process disclosed in our co-pending application;
- adding the said proprietary composition in a suitable manner to get the Water beverage ready to fill and pack as required.

The process has been designed to meet the specific requirements of the beverage of the present invention.

This process is unique as it involves effective treatment and sterilization of water without having to use chemicals or long storage. This on line treatment reduces the risks of the water and also provides a consistent base characteristic on which the blend can enhance to achieve the desired nutritional characteristics. This treatment of source water involves filtration, ozonization, and deozonization before filtration through reverse osmosis. Permeate is UV sterilized and then used as a solvent for the composition. This on line treatment reduces the risks of the water and also provides a consistent base characteristic on which the composition can enhance to achieve the desired nutritional characteristics. The compositioned beverage is filled and packed as required.

The limitation or disadvantage of this composition in terms of its restricted use to
 (i) Food products only as a means of fortification.
The limitation or disadvantage of this product relates to—
 (i) Form of ingestion.

The invention will now be explained with the help of following examples. However, the scope of the invention should not be limited to these examples as the person skilled in the art can easily vary the proportion of the ingredients and combinations.

Example 1

Preparation of the Zinc Fortifying Composition for Health
 Two different packages (one dry parts & one Liquid part) is prepared for the batch of 25000 liters.
0.6626 Kg of Dry Part Comprises:
 0.4125 kg of Zinc Lactate Gluconate
 0.25 kg of Potassium Sorbate
These ingredients are carefully weighed, blended and packaged in a sterile & dry container for use at the manufacturing facility. The specification sheets are maintained and the dry part has to meet the specifications at the manufacturing location before these are used for the preparation of the concentrate.
0.5375 Of Liquid Part Comprises:
 0.5375 kg of Copper Ion Source
The ingredient is carefully weighed and packaged in a sterile & dry container for use at the manufacturing facility. The specification sheets are maintained and the liquid part has to meet the specifications at the manufacturing location before these are used for the preparation of the concentrate.

Example 2

Preparation of the Zinc Fortified Water Beverage with Fortifying Composition for Health
 A blending tank of 225 liters is taken for making the concentrate. 200 liters of treated water is made available in the blending tank. The dry part is added to the water in the blending tank. The stirring operations are carried out for 15 mins. The liquid part is added while the stirring is maintained. Treated Water is then added to make the volume of concentrate in the tank to 225 liters. Dosing operation is then carried out to make the fortified Zinc product.

We claim:
1. A zinc and copper fortifying composition for the fortification of food products, the zinc and copper fortifying composition comprising:
 about 32.25% to 34.37% by weight zinc lactate gluconate;
 about 42.5% to 45.2% by weight copper ion source; and
 about 18% to 22% by weight class II preservative.
2. The zinc and copper fortifying composition as claimed in claim 1, wherein the zinc lactate gluconate is present in an amount of 34.37% by weight.
3. The zinc and copper fortifying composition as claimed in claim 1, wherein the copper ion source is present in an amount of 44.79% by weight.
4. The zinc and copper fortifying composition as claimed in claim 1, wherein the class II preservative is present in an amount of 20.83% by weight.
5. The zinc and copper fortifying composition as claimed in claim 1, wherein the copper ion source comprises copper sulfate.
6. The zinc and copper fortifying composition as claimed in claim 1, wherein the class II preservative is potassium sorbate.
7. The zinc and copper fortifying composition as claimed in claim 1, wherein the copper ion source comprises ammonium sulfate.
8. The zinc and copper fortifying composition as claimed in claim 1, wherein the copper ion source comprises an acidic compound.
9. A zinc and copper fortifying composition for the fortification of food products, the zinc and copper fortifying composition comprising:
 34.37% by weight zinc lactate gluconate;
 44.79% by weight copper ion source; and
 20.83% by weight class II preservative.
10. The zinc and copper fortifying composition as claimed in claim 9, wherein the copper ion source comprises copper sulfate.
11. The zinc and copper fortifying composition as claimed in claim 9, wherein the class II preservative is potassium sorbate.
12. The zinc and copper fortifying composition as claimed in claim 9, wherein the copper ion source comprises ammonium sulfate.
13. The zinc and copper fortifying composition as claimed in claim 9, wherein the copper ion source comprises an acidic compound.

* * * * *